(12) United States Patent
Hildenbrandt et al.

(10) Patent No.: US 10,411,682 B2
(45) Date of Patent: Sep. 10, 2019

(54) METHODS OF AND APPARATUS FOR DETERMINING PARTICLE INCLUSION AND SIZE IN MOLTEN METAL

(71) Applicant: NOVELIS INC., Atlanta, GA (US)

(72) Inventors: Leslie Calvin Hildenbrandt, Windsor, CO (US); Gary Thornton, Fort Collins, CO (US)

(73) Assignee: Novelis Inc., Atlanta, GA (US)

( * ) Notice: Subject to any disclaimer, the term of this patent is extended or adjusted under 35 U.S.C. 154(b) by 584 days.

(21) Appl. No.: 14/203,335

(22) Filed: Mar. 10, 2014

(65) Prior Publication Data

US 2014/0266316 A1  Sep. 18, 2014

Related U.S. Application Data

(60) Provisional application No. 61/778,044, filed on Mar. 12, 2013.

(51) Int. Cl.
*H03K 5/125* (2006.01)
*G01N 27/416* (2006.01)
*G01N 33/205* (2019.01)

(52) U.S. Cl.
CPC .......... *H03K 5/125* (2013.01); *G01N 27/4161* (2013.01); *G01N 33/205* (2019.01)

(58) Field of Classification Search
CPC ..................... H03K 5/125; G01N 27/4161
See application file for complete search history.

(56) References Cited

U.S. PATENT DOCUMENTS

| | | |
|---|---|---|
| 3,389,335 A | 6/1968 | Claps et al. |
| 4,450,435 A | 5/1984 | James |
| 4,555,662 A | 11/1985 | Doutre et al. |
| 4,600,880 A | 7/1986 | Doutre et al. |
| 4,775,833 A | 10/1988 | Roos et al. |
| 4,810,911 A | 3/1989 | Noguchi |

(Continued)

FOREIGN PATENT DOCUMENTS

AU  2010235916 A1 * 11/2010 ........... G01N 33/206

OTHER PUBLICATIONS

Draganovici, "A user-friendly software interface for the liquid metal cleanliness analyzer (LiMCA)," Thesis, 1994, Canada/McGill University, 4 pages.

(Continued)

*Primary Examiner* — Jennifer E Simmons
(74) *Attorney, Agent, or Firm* — Kilpatrick Townsend & Stockton LLP

(57) ABSTRACT

Methods and apparatus for measuring the cleanliness of molten metal. Direct current is passed through molten metal advancing through a passage. A voltage signal is analyzed for the presence of solid generally non-metallic inclusions in the metal. A method includes sampling digital data of the voltage signal to generate data samples; updating a delayed running average of the data samples to establish a baseline for identifying sudden changes in amplitude of the data samples; determining a threshold by adding a prescribed value to the baseline; identifying a possible inclusion when a significant number of data samples exceeds the threshold; storing a maximum count as the data samples using peak detection until a prescribed number of the data samples fall below the threshold; and comparing a parameter of the possible inclusion with a lookup table to categorize the possible inclusion as either (i) an actual inclusion or (ii) noise.

20 Claims, 10 Drawing Sheets

(56) References Cited

U.S. PATENT DOCUMENTS

| | | | |
|---|---|---|---|
| 5,039,935 | A | 8/1991 | Hachey et al. |
| 5,130,639 | A | 7/1992 | Hachey |
| 5,130,883 | A * | 7/1992 | Edwards ............ H03K 17/0822 |
| | | | 307/64 |
| 5,896,113 | A | 4/1999 | O'Neill, Jr. |
| 7,459,896 | B2 | 12/2008 | Marcotte et al. |
| 7,466,156 | B2 | 12/2008 | Marsh et al. |
| 7,752,953 | B2 | 7/2010 | Sokol et al. |
| 7,768,292 | B1 * | 8/2010 | Koch ..................... G01R 31/40 |
| | | | 324/764.01 |
| 7,780,906 | B2 | 8/2010 | Burty et al. |
| 7,942,950 | B2 | 5/2011 | Burty et al. |
| 7,972,950 | B2 | 7/2011 | Na et al. |
| 9,389,164 | B2 | 7/2016 | Thornton |
| 2001/0005130 | A1 | 6/2001 | Manzini et al. |
| 2002/0067155 | A1 | 6/2002 | Conti et al. |
| 2004/0201371 | A1 | 10/2004 | Conti |
| 2005/0231185 | A1 | 10/2005 | Marcotte et al. |
| 2006/0192433 | A1 * | 8/2006 | Fuglevand ............... H02J 7/345 |
| | | | 307/64 |
| 2012/0113047 | A1 * | 5/2012 | Hanauer ............... G06F 3/0416 |
| | | | 345/174 |
| 2015/0253267 | A1 * | 9/2015 | Quellet ............. G06Q 10/0637 |
| | | | 324/76.39 |

OTHER PUBLICATIONS

Carozza, "Water Modelling of Particle Discrimination Using LiMCA Technology," Thesis, Sep. 1999, Canada/McGill University, 12 pages.

Badowski et al., "Measurement of Non-Metallic Inclusions in the Size Range of 10-20µm by LiMCA," Light Metals 2012, 2012, pp. 1077-1083, TMS (The Mineral, Metals & Materials Society), 7 pages.

Autosignal, "Cutting Edge Signal Analysis Software," 2013, http://www.sigmaplot.com/products/autosignal/autosignal.php, AutoSignal: Cutting Edge Signal Analysis Software by Systat Software, 2 pages.

Jung, Do Yang, "Shield Ultracapacitor Strings From Overvoltage Yet Maintain Efficiency," Electronic Design, May 27, 2002, http://electronicdesign.com/components/shield-ultracapacitor-strings-overvoltage-yet-maintain-efficiency, Penton Media, Inc., 3 pages.

Miller, John M., et al., "Carbon-Carbon Ultracapacitor Equivalent Circuit Model, Parameter Extraction, and Application", Slide 39, Oct. 18, 2007, Ansoft Ansoft Frist Pass Workshop, Southfield, Michigan, 2 pages.

"IRF1324S-7PPbF HEXFET Power MOSFET," Specifications Datasheet, Dec. 21, 2010, International Rectifier, El Segundo, California, 9 pages.

International Patent Application No. PCT/US2014/022768, International Search Report and Written Opinion dated Jun. 3, 2014, 11 pages.

International Patent Application No. PCT/US2014/022822, International Search Report and Written Opinion dated Aug. 14, 2014, 9 pages.

Canadian Patent Application No. CA 2,896,727, Office Action dated Jul. 26, 2018, 5 pages.

Office Action issued in Canadian Patent Application No. 2,896,727 dated May 1, 2019, 4 pages.

* cited by examiner

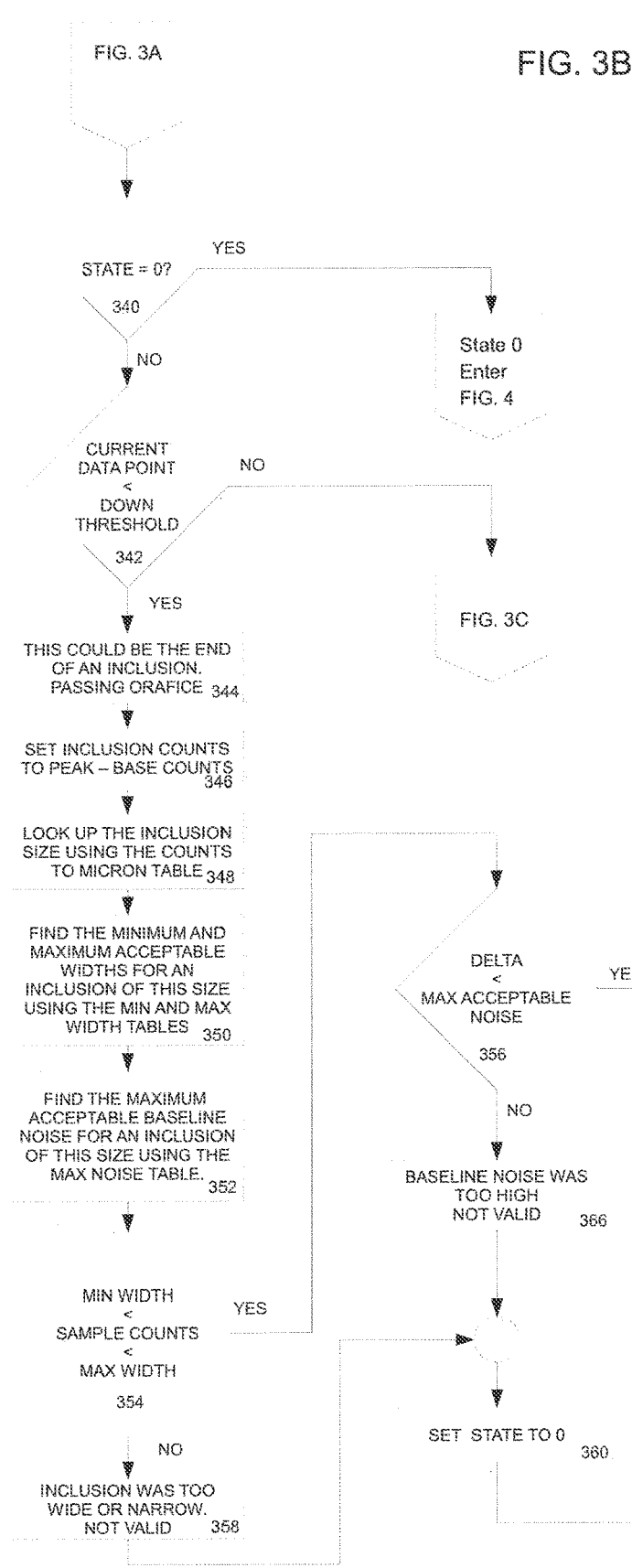

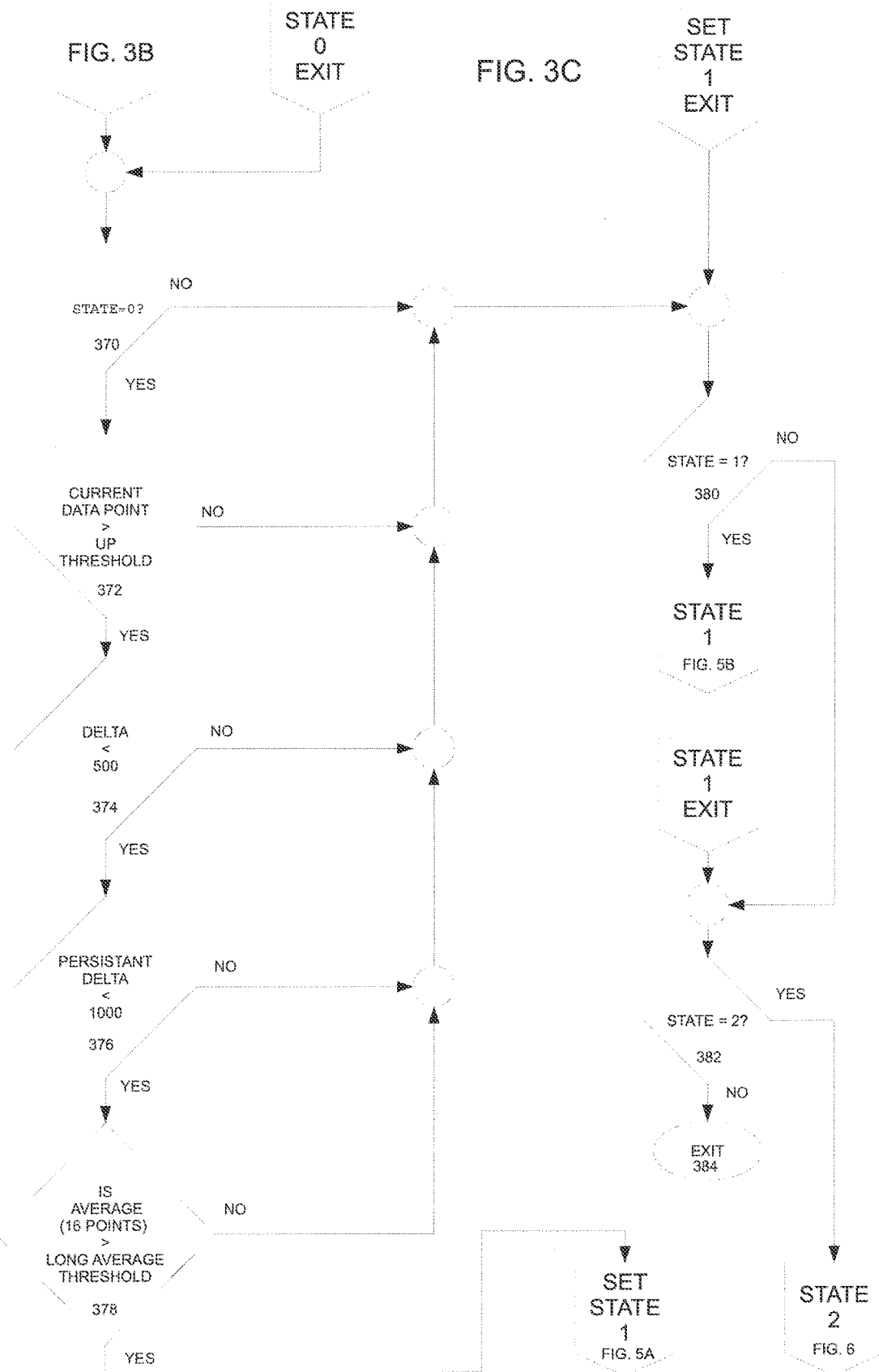

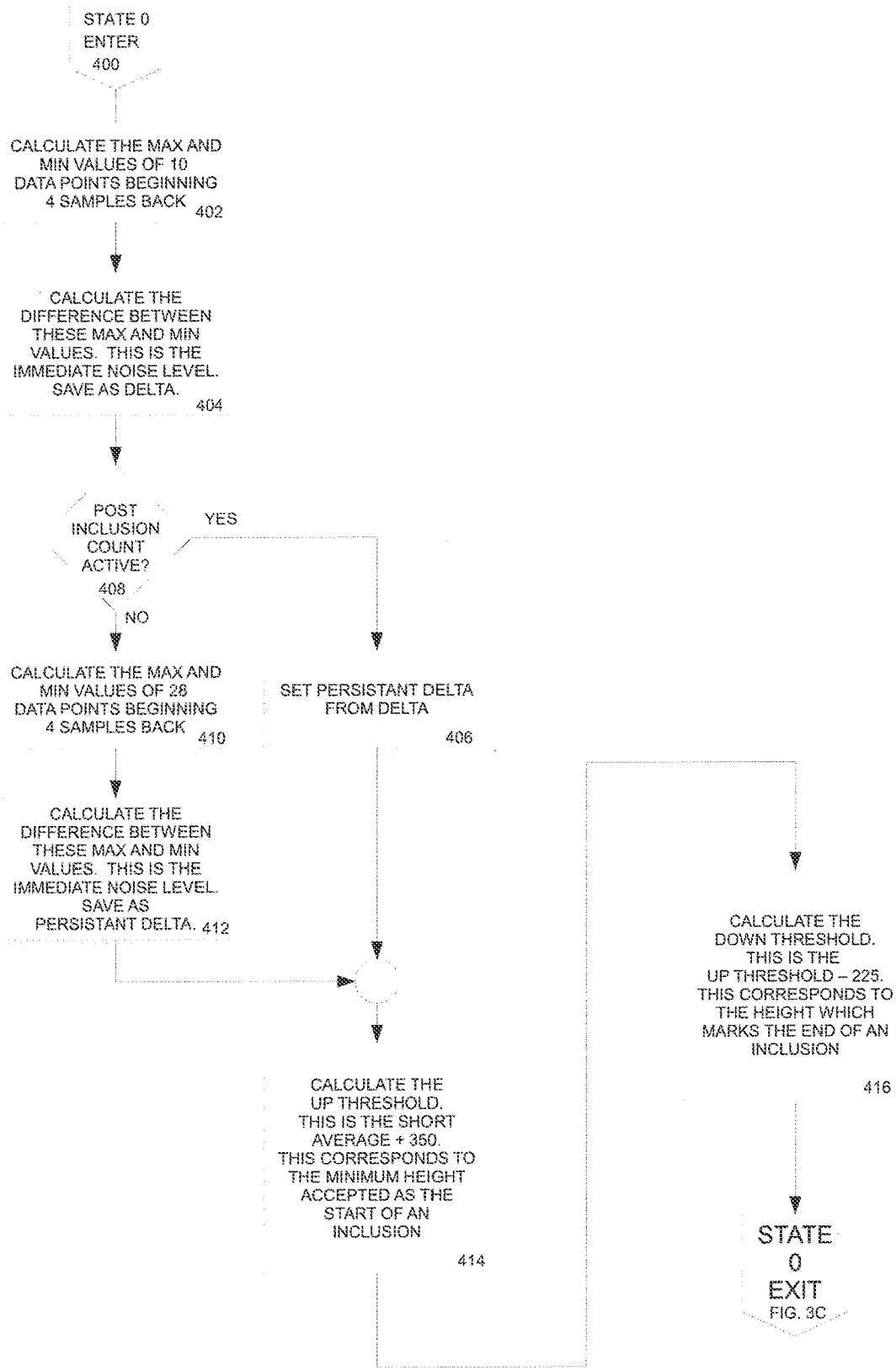

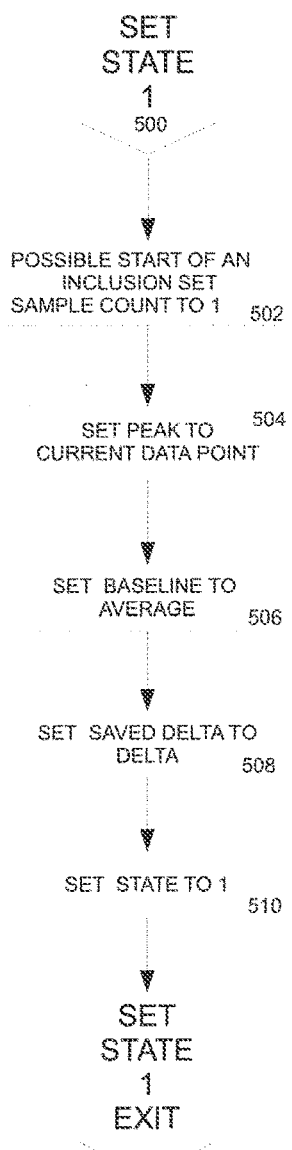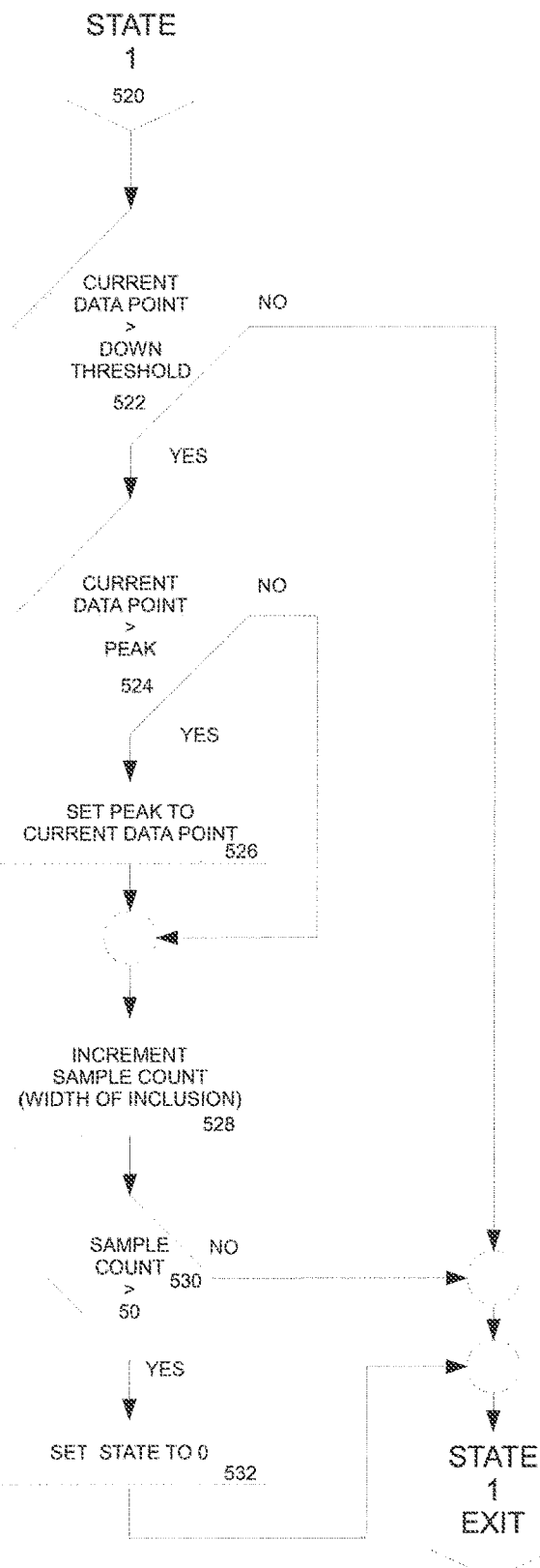

METHODS OF AND APPARATUS FOR DETERMINING PARTICLE INCLUSION AND SIZE IN MOLTEN METAL

RELATED APPLICATION

This application claims the benefit of U.S. Provisional Patent Application Ser. No. 61/778,044 filed Mar. 12, 2013, the entire contents of which are incorporated by reference.

FIELD OF THE INVENTION

This invention relates to methods of and apparatus for determining the presence or absence of solid and generally non-metallic inclusions within molten metal including determining size and concentration information of such inclusions.

BACKGROUND OF THE INVENTION

Molten metals, particularly molten aluminum and molten steel, are frequently contaminated by entrained small non-metallic inclusions that give rise to a variety of shortcomings or defects in products manufactured from the molten metal. For example, such inclusions may cause the solidified metal to tear during mechanical working operations, or may introduce pin-holes and streaks in foils and surface defects and blisters into sheets, or give rise to increased rates of breakage during the production of metal wire, etc.

A known analyzer that enables quick measurements of metal cleanliness and provides size and concentration information of the inclusions is the so-called Liquid Metal Cleanliness Analyzer (often abbreviated to "LiMCA"). A conventional LiMCA apparatus may comprise a probe having an electrically-insulating wall means, often in the form of a sampling tube, having a small precisely-dimensioned passage in a side wall. The tube is immersed in the molten metal to be tested and a uniform stream of the metal is drawn by vacuum or pressure through the small passage while a substantially constant electric current is passed through the stream between electrodes disposed respectively inside and outside the tube. The particulate inclusions generally have very high electrical resistivity compared to the molten metal and the travel of a particle through the passage is accompanied by a change in resistance for the electric current within the passage, thereby producing an electrical pulse in the voltage across the electrodes. The number of pulses produced while a fixed volume of metal transits the passage provides an indication of the number of particles per unit volume present within the metal. Furthermore, it is possible to analyze the pulse to determine particle size and size distribution. Generally, the voltage is monitored in real time, but the voltage trace may be recorded and analyzed afterwards and kept for future referral. Examples of typical LiMCA devices are described in U.S. Pat. Nos. 4,600,880, 5,130,639, 4,555,662, and 5,039,935.

For LiMCA apparatus to work effectively, the current flowing between the electrodes must be direct current (DC) and must be kept fairly constant for a sufficient period of time, e.g. 30 seconds or so, to allow for a reliable measurement. Also, the current passing between the electrodes must be kept fairly high, and it is desirable to minimize random electrical noise that can undesirably obscure the desired voltage signal. To meet these requirements, it has been usual to provide the apparatus with one or more rechargeable batteries (for example of the Nickel-Cadmium type), to generate the required DC current during the testing phase. The batteries are recharged between the test cycles when the generation of electrical noise is not important, e.g. using a mains generator or battery recharger. While the use of batteries as the current source can be effective, batteries take a significant time to recharge and require additional equipment to ensure that the recharging takes place properly. They also tend to be heavy, bulky and may have a short operational life if constantly subjected to rapid discharge and recharge cycles. Another problem that conventional apparatus may encounter is the generation of considerable heat, representing a loss of efficiency and requiring extra size and weight for cooling devices or heat sinks.

The use of ultra-capacitors, rather than batteries, as power sources for LiMCA devices has been disclosed in U.S. Pat. No. 7,459,896 which issued to Marcotte et al. on Dec. 2, 2008 ("the Marcotte et al. patent") (the disclosure of which patent is specifically incorporated herein by this reference). As explained in this patent, ultra-capacitors can be employed as power sources as an alternative to rechargeable batteries. However, ultra-capacitors have a lower volume charge density than rechargeable batteries and cannot therefore supply high currents at constant rates for extended periods of time. In the device of the Marcotte et al. patent, the use of an ultra-capacitor can result in the generation of significant heat and require circuitry that is susceptible to inclusion of electrical noise. This has necessitated complex measures for eliminating noise from the test signal, e.g. by providing three or more electrodes to generate a reference signal for comparison purposes. There is therefore a desire for alternative approaches that enable the use of ultra-capacitors as a current source without attendant disadvantages.

Previous LiMCA designs, particularly those incorporating batteries, have generally employed large ballast resistors and transistors operating in a linear (intermediate) region to maintain steady current generating high heat losses and requiring heat management to keep operating temperatures within a safe region.

It has also been known to incorporate into the apparatus some means of reducing noise in the voltage signal so that the wanted pulses can be detected more reliably. For example, Marcotte et al. employ a three-electrode design to generate an additional signal containing only noise, and then subtracting the signals from each other to reduce the background noise signal.

However, while effective, this increases the size and cost of the apparatus and requires additional circuitry.

There is therefore a need for alternative designs and methods of use of LiMCA equipment.

SUMMARY OF THE INVENTION

Exemplary embodiments of the present invention employ a method comprising: (a) sampling digital data of measured voltage across electrodes partially immersed in a molten metal to generate data samples; (b) updating a delayed running average of the data samples to establish a baseline for identifying sudden changes in amplitude of the data samples; (c) determining a threshold by adding a prescribed value to the baseline; (d) identifying a possible inclusion when a significant number of data samples exceeds the threshold; (e) storing a maximum count as the data samples using peak detection until a prescribed number of the data samples fall below the threshold; and (f) comparing a parameter of the possible inclusion with a lookup table to categorize the possible inclusion as either (i) an actual inclusion or (ii) noise.

In particular embodiments of the above method, the parameter may include width, the data points of the validated inclusions from step (f) may be saved, a noise level present in the baseline established at step (b) may be monitored, whereupon the noise level in the baseline preceding the possible inclusion after identification at step (d) may also be monitored, and a maximum acceptable noise level based on the width of the actual inclusion may be dynamically adjusted.

In another exemplary embodiment of the method, the measured voltage across the electrodes partially immersed in a molten metal may be obtained by charging at least one ultra-capacitor to a voltage of 2.7 volts or less; advancing molten metal through a passage in a wall made of electrically resistive material between an interior and an exterior of a metal cleanliness probe; discharging the at least one ultra-capacitor, via a resistor ladder network circuit associated with the or each ultra-capacitor, through the molten metal advancing through the passage between an interior electrode positioned in the interior of the probe and an exterior electrode positioned outside the probe, wherein the or each resistor ladder network circuit comprises two or more resistors connected in parallel to each other, each resistor being in a circuit leg including one or more field effect transistors capable of being switched directly between a nonconductive OFF condition and a fully conductive ON condition, the resistor ladder network having resistance values effective to maintain a measurement current of no more than 100 amps through the molten metal advancing through the passage; switching the field effect transistors of the circuit legs of the or each resistor ladder network circuit between the nonconductive OFF condition and the fully conductive ON condition according to a sequence for maintaining the measurement current within a pre-determined current range at least for a time required for measurement of cleanliness of the molten metal; and measuring the voltage across the internal and external electrodes.

Exemplary embodiments of the present invention may also employ a computer-readable non-transitory storage medium storing statements and instructions, which, when executed by one or more processors, cause the one or more processors to: sample digital data of measured voltage across electrodes partially immersed in a molten metal to generate data samples; update a delayed running average of the data samples to establish a baseline for identifying sudden changes in amplitude of the data samples; determine a threshold by adding a prescribed value to the baseline; identify a possible inclusion when a significant number of data samples exceeds the threshold; store a maximum count as the data samples using peak detection until a prescribed number of the data samples fall below the threshold; and compare a parameter of the possible inclusion with a lookup table to categorize the possible inclusion as either (i) an actual inclusion or (ii) noise.

Other exemplary embodiments may provide apparatus for measuring cleanliness of a molten metal. Such apparatus may comprise one or more rechargeable ultra-capacitors operable at a discharge voltage of 2.7 volts or less; at least two electrodes; a metal cleanliness probe having an interior, a wall made of electrically resistive material and a passage in the wall interconnecting the interior with an exterior of the probe to allow molten metal to pass therethrough, wherein one of the at least two electrodes is positioned in the interior of the probe as an interior electrode and another of the at least two electrodes is positioned outside the probe as an exterior electrode; a device measuring voltage across the interior and exterior electrodes and generating a voltage signal; for the or for each of the one or more ultra-capacitors, an associated resistor ladder network circuit interconnecting its associated ultra-capacitor with one of the electrodes, the or each resistor ladder network circuit comprising two or more resistors connected in parallel to each other, each resistor being in a circuit leg including one or more field effect transistors capable of being switched directly between a nonconductive OFF condition and a fully conductive ON condition, and the resistor ladder network circuit or circuits having resistance values effective to maintain a measurement current of no more than 100 amps through molten metal present in the passage when the circuit or circuits are exposed to the discharge voltage from the one or more ultra-capacitors; a controller adapted for individually switching the field effect transistors of the circuit legs of the or each resistor ladder network circuit between the nonconductive OFF condition and the fully conductive ON condition according to a sequence effective for maintaining the measurement current within a pre-determined current range at least for a time required for measurement of cleanliness of the molten metal; and an analyzer for analyzing the voltage signal. The analyzer of such apparatus comprises a computer-readable non-transitory storage medium storing statements and instructions, which, when executed by one or more processors, cause the one or more processors to: (a) sample digital data of measured voltage across the electrodes to generate data samples; (b) update a delayed running average of the data samples to establish a baseline for identifying sudden changes in amplitude of the data samples; (c) determine a threshold by adding a prescribed value to the baseline established in step (b); (d) identify a possible inclusion when a significant number of data samples exceeds the threshold determined in step (c); (e) store a maximum count as the data samples using peak detection until a prescribed number of the data samples fall below the threshold established in step (c); and (f) compare a parameter of the possible inclusion with a lookup table to categorize the possible inclusion as either (i) an actual inclusion or (ii) noise.

There may be a single ultra-capacitor and associated resistor ladder network circuit, but alternatively there may be two or more such ultra-capacitors and circuits to reduce the current carried by each resistor circuit, although it will be recognized that the "footprint" of the apparatus required when two, or more especially more than two, of such ultra-capacitors and circuits are provided likely increases the size and cost of the apparatus.

In one exemplary form, the field effect transistor or transistors of each or most of the circuit legs are surface mounted field effect transistors that employ minimum space in the apparatus and avoid undue susceptibility to noise. Such FETs have component bodies that are directly attached to an underlying circuit board and have projecting terminals that are connected to the circuit paths of the circuit board without requiring the presence of holes in the circuit board. Such FETs may have very low resistance in the fully conductive ON condition and, when subjected to relatively low voltages (i.e. 2.7 volts, and alternatively 1.4 volts, or less) in a resistor ladder network circuit, generate little heat, so there is usually no need to provide the FETs with bulky and heavy heat sinks conventionally used for FETs of other kinds. Moreover, by mounting the FETs directly onto the circuit board, the use of elongated leads is not required, and this reduces the amount of random noise picked up by the devices since such leads act as small antennas. In exemplary embodiments, the FETs are switched directly from nonconductive OFF condition to the fully-conductive ON condition in a very short period of time (e.g. typically less than 1 μs). Suitable FETs of this kind may be obtained, for example, from International Rectifier of El Segundo, Calif. 90245, USA, or Digi-Key Corporation of Thief River Falls, Minn. 56701, USA.

In one exemplary embodiment, the field effect transistor or transistors of each of the circuit legs may be chosen to introduce a resistance of less than 1 milli-ohm into the circuit leg when in the fully conductive ON condition, thus minimizing heat loss in the circuit. Such minimal resistance values may also be achieved by providing two or more field effect transistors connected in parallel in a circuit leg, thereby reducing the combined resistance introduced by the field effect transistors into the circuit leg. This allows the use of field effect transistors that may have a higher resistance in the ON condition than would be desired for individual use.

The use of surface-mounted FETs enables the design to be made compact, and the compact circuitry reduces noise in the voltage signal that makes it possible to determine the metal cleanliness from the voltage signal while employing only two electrodes, i.e. without having to provide additional electrodes and circuitry for noise-elimination purposes.

A particular exemplary embodiment employs two ultra-capacitors and two separate resistor ladder network circuits. This reduces the current flow in each network circuit to half what it would have been if using a single ultra-capacitor and a single resistor ladder network circuit. This allows each circuit to stay cooler during the measurement period. Each ultra-capacitor then provides half of the current required. For example, if the apparatus requires a measurement current of 60-65 amps, each ultra-capacitor and resistor ladder network circuit would provide 30-32.5 amps, each circuit being connected to the electrodes to provide current flow in the same direction. Of course, more than two ultra-capacitors and resistor network circuits could be employed in this way, but with a consequent need for additional capital and size requirements.

The resistors of each resistor ladder network circuit may have resistance values that differ from each other. The controller may then be programmed to switch the field effect transistors of the circuit legs to first turn on a circuit leg of lowest resistance, and then to turn on one or more circuit legs of higher resistance as the discharge voltage of the associated ultra-capacitor declines during the time required for measurement. When there are three or more circuit legs per resistor ladder network circuit, the controller may be programmed to turn on the circuit legs according to a binary sequence effective to maintain the measurement current within the predetermined current range.

The resistors employed in the resistor ladder network may individually be of low resistance values for example, in one exemplary embodiment, within a range of 0.02 to 2.64 ohms, or alternatively within a range of 0.02 to 0.66 ohms.

The apparatus may further include a device for measuring the measurement current and for generating a signal alerting the controller when the current falls to a lower limit of the predetermined current range, so that the controller can then switch FETs on and/or off to maintain the measurement current within the pre-determined range. The apparatus may also include a voltage signal analyzer adapted to determine metal cleanliness from the signal from the device registering voltage, and one or more chargers for charging the ultra-capacitor(s) between metal cleanliness measurements.

The apparatus in one exemplary embodiment may include circuitry for purging the passageway of debris and scale prior to cleanliness measurements. In one form, this may take the form of a switchable circuit by-passing the resistor ladder network circuit and connecting the or each ultra-capacitor in parallel directly across the interior and exterior electrode for purging the passage. For higher purging currents, the apparatus may include a switchable circuit connecting two or more ultra-capacitors in series and by-passing the resistor ladder network circuits to connect the series-connected ultra-capacitors across the interior and exterior electrodes. The higher voltage of the series-connected ultra-capacitors produces a higher current through the passage than an alternative form in which two or more ultra-capacitors are connected in parallel.

In one exemplary form, the apparatus may employ two, and no more than two, electrodes, i.e. a single internal electrode and a single external electrode. This is because the resistance of the exemplary apparatus to noise pick-up may enable the resulting voltage signal to be analyzed without elaborate noise-cancellation equipment. The resistance to noise may be improved in particular by positioning the resistors and surface mounted field effect transistors on the same circuit board immediately adjacent to each other, thereby minimizing the footprint of the circuit components and the lengths of connectors. A combination of features also makes it possible to largely avoid the presence of heat sinks conventionally used to withdraw heat from resistors and field effect transistors because these elements may run quite cool (e.g. cool enough to touch). This is possible because of one or more features, such as a low discharge voltage of the ultra-capacitors, a low resistance of the field effect transistors in the ON condition, a relatively low measurement current, low resistance values of the resistors, etc., as discussed.

In one exemplary form, each resistor ladder network circuit has three or more circuit legs (generally up to six) and the individual switching of the field effect transistors of the circuit legs of the or each resistor ladder network ladder circuit is carried out according to a binary sequence to maintain the measurement current within the pre-determined current range. The sequence may be pre-determined according to a calibration routine and recorded for use during the time required for measurement of cleanliness of the molten metal. In one form, the field effect transistors are switched from the OFF to the ON condition by voltage signals generated by a controller, e.g. an electronic circuit containing a micro-processor and optionally a memory device and timer.

If desired, the passage may be purged before the time required for measurement of cleanliness of the molten metal by directing current from the at least one ultra-capacitor through molten metal in the passage while causing the current to by-pass the or each resistor ladder network circuit. In one exemplary form, two or more of the ultra-capacitors are connected in series so that an increased voltage may be applied across the electrodes as the series-connected ultra-capacitors are discharged through the passage.

Exemplary apparatus embodiments of the invention may be made quite compact because heat generation is kept to a minimum by limiting the operational voltage of the ultra-capacitor to no more than 2.7 volts (e.g. less than 1.4 volts, such as within a range of 0.8 to 1.4 volts), by limiting the measurement current to no more than 100 amps, and by employing FETs that have low resistance when in the fully conductive ON conditions, e.g. no more than a few milli-ohms and, for example, no more than 1 milli-ohm. As noted above, FETs with higher resistance may be employed with the same effect if two or more are connected in parallel within a leg of the circuit.

In exemplary embodiments, the resistor ladder circuit network provides a way of employing FETs without resorting to operation of such devices in their intermediate ranges that generate significant heat. Thus, the devices may be used only the non-conductive OFF condition and the fully conductive ON condition that generate almost no losses. There is then very little heat generated by the FETs or the resistors and the need for bulky and heavy heat sinks can be avoided. As previously noted, this also makes it possible to use surface mounted FETs, which take up less space and are less susceptible to reception of electrical noise.

By adjusting ladder resistor values, ultra-capacitor charge voltage, calibration parameters, and/or control set points (e.g. via firmware), exemplary embodiments can be adjusted for sampling in different metals and can be adjusted for higher or lower discharge currents and tighter or looser current ripple (i.e. range between maximum and minimum currents during sampling).

BRIEF DESCRIPTION OF THE DRAWINGS

Exemplary embodiments of the present invention are described in detail below in conjunction with the accompanying drawings, in which:

FIGS. 3A, 3B and 3C are flow charts illustrating an exemplary embodiment of the present invention;

FIG. 4 is a flow chart illustrating one operating state process according to an exemplary embodiment of the present invention;

FIGS. 5A and 5B are flow charts illustrating another operating state according to exemplary embodiments of the present invention;

FIG. 7 is a graph showing the results of a test carried out according to the method of FIG. 3; and.

DETAILED DESCRIPTION

Figure 1:
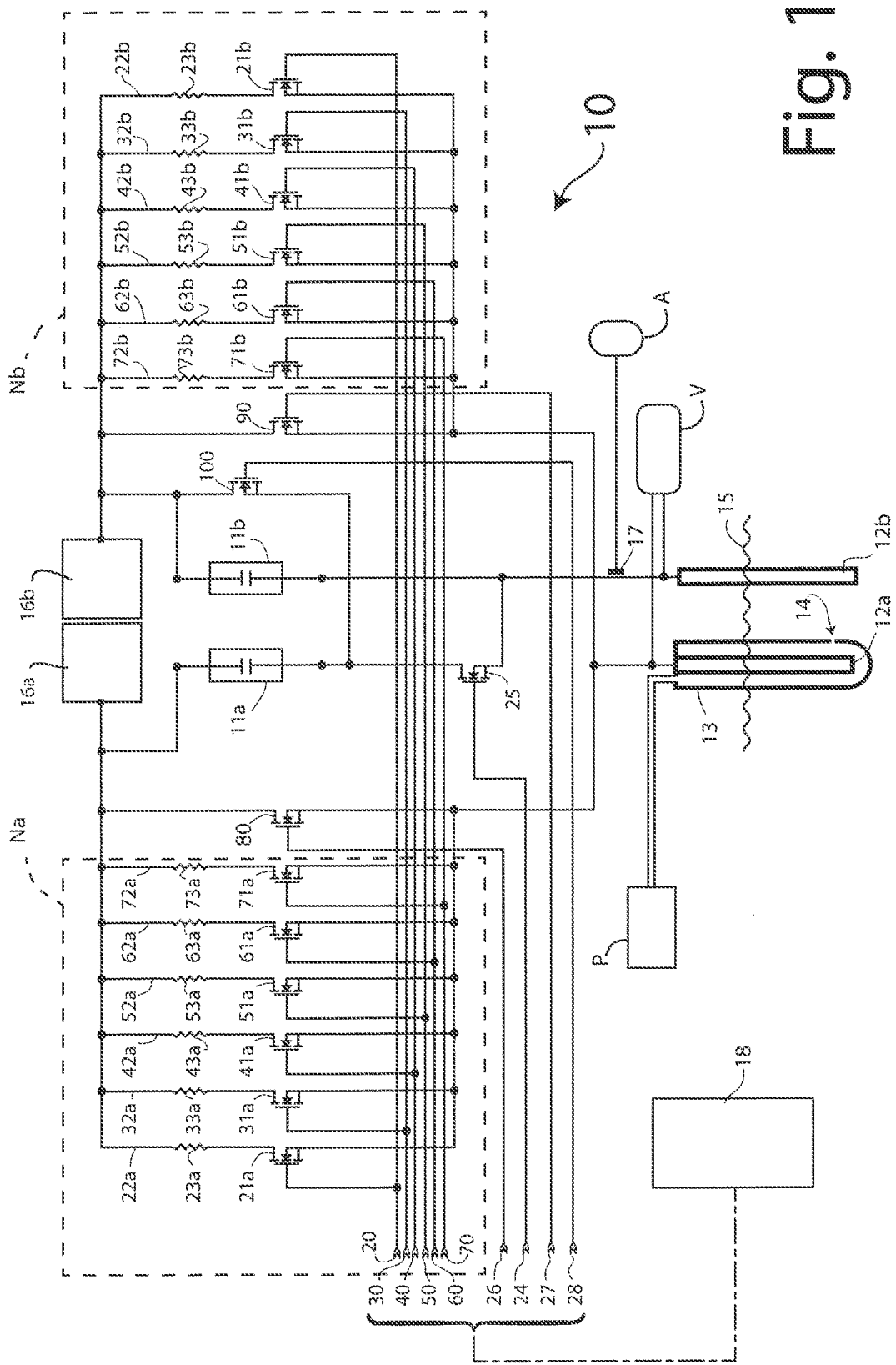
FIG. 1 is a combined circuit diagram and schematic sketch illustrating an exemplary embodiment of the present invention.

FIG. 1 shows a circuit diagram 10 suitable for supplying cleanliness-measurement current in a LiMCA analyzer according to one exemplary embodiment of the invention. This circuit, or at least the majority of it, may be provided on a circuit board referred to as a "power board." The apparatus may also include a "main board" containing equipment for initiating a calibration routine, and an "analog board" containing measuring, recording and possibly signal processing devices. For convenience, the main board may be remote from the power board and analog board, e.g. located in a control case (not shown) connected to the power board in a probe unit by an umbilical cable of suitable length (for example, thirty feet in length). The analog board is preferably positioned as close as possible to the power board for minimal susceptibility to noise.

In the circuit diagram 10, two ultra-capacitors 11a and 11b are provided to supply direct current ultimately to electrodes 12a (positive) and 12b (negative) during a measurement period of the apparatus. The electrodes are positioned on opposite sides of a wall of an enclosed hollow tubular probe 13 made of electrically resistive material having a small passage 14 therein such that the electrode 12a is internal of the probe and electrode 12b is external of the probe. The probe 13 and the external electrode 12b are immersed in molten metal to be analyzed (represented by wavy surface line 15). Before the measurement period begins, the ultra-capacitors 11a and 11b are each charged by associated charging devices 16a and 16b up to a voltage at which they are capable, together, of delivering a predetermined measurement current, in one embodiment at least 65 amps, but no more than 100 amps, when the measurement period begins. The maximum charging voltage is kept low compared voltages at which ultra-capacitors normally operate, e.g. a maximum of 2.7 volts and generally in the range of 0.8 to 1.4 volts. The charging devices 16a, 16b and accompanying circuitry are turned off before and at all times during the measurement period to prevent electrical noise generation from AC circuits and the like used by such devices. The use of such low voltages contributes to the desired low heat losses.

The positive terminals of the ultra-capacitors 11a and 11b are each connected to the internal electrode 12a via separate resistor ladder network circuits Na and Nb switchable by field effect transistors (FETs), all of which are of the surface mounted type to allow for a compact design (i.e. they are mounted in direct contact with a supporting circuit board). The negative terminals of both ultra-capacitors 16a, 16b are connected to electrode 12b when FET 25 is turned on.

To commence a measurement operation, a vacuum pump P (or alternatively a vacuum reservoir) withdraws air from the interior of the probe 13 and the resultant vacuum draws molten metal at a constant rate into the probe interior through the narrow passage 14. A control voltage is applied through line 20 to FETs 21a and 21b to turn on the circuits 22a and 22b (referred to as circuit "legs" of the resistor ladder network circuits) leading from the positive terminals of the ultra-capacitors 11a and 11b, respectively, thereby allowing connection to the positive electrode 12a. The circuit legs 22a and 22b contain ballast resistors 23a and 23b, respectively, of the same resistance value suitable for allowing a combined current through the metal of no more than 100 amps, and preferably 65 to 70 amps. At the same time, a control voltage is applied via line 24 to FET 25 to turn on the FET and thus connect the negative terminal of ultra-capacitor 11a to the negative electrode 12b to complete the circuit. The negative electrode of ultra-capacitor 11b is constantly connected to the negative electrode 12b, so at this stage both ultra-capacitors supply current through the metal in passage 14 via the electrodes 12a and 12b. As the current flows through the metal, the voltage across the electrodes is measured by a device registering voltage and producing a voltage signal, e.g. a voltage recording and analyzing apparatus V, so that the presence and characteristics of pulses in the voltage signal that are characteristic of metal inclusions can be detected, measured, assessed and determined.

As the testing operation proceeds, the output voltages of the ultra-capacitors 11a and 11b rapidly decay, so the current passing through the metal in passage 14, measured for example by a current-measuring device 17 (e.g. a Hall-effect transducer) and viewed or recorded by current meter A, starts to decline from the desired initial value of 65-70 amps. To compensate for this decline, and to maintain the current in a predetermined measurement range of, for example, approximately 60 to 65A, one or more additional ladder network "legs" 32a/32b, 42a/42b, 52a/52b, 62a/62b and 72a/72b of the ladder network circuits are activated (turned on), so that current may flow respectively through resistor pairs 33a/33b, 43a/43b, 53a/53b, 63a/63b and/or 73a/73b to reduce the overall resistance in the ladder network circuits between the ultra-capacitors and the internal electrode 12a. This is achieved by applying control voltages via lines 30, 40, 50, 60 and 70 as required to FET pairs 31a/31b, 41a/41b, 51a/51b, 61a/61b and 71a/71b, respectively. The application of such control voltages is under the control of a FET controller 18 which may comprise a micro-processor device.

The sequence in which such FETs are turned on is chosen to maintain the measurement current always within the desired range, e.g. approximately 55 to 65 amps, or alternatively approximately 60 to 65 amps, as the voltage of the ultra-capacitors 11a, 11b decays. In a particular example of the illustrated circuit, if resistors 23a/23b are each said to have a resistance value of "R", resistors 33a/33b preferably each have a resistance value of 2×R, resistors 43a/43b preferably each have resistance value of 4×R, resistors 53a/53b preferably each have a resistance value of 8×R, resistors 63a/63b preferably each have a resistance value of 16×R and resistors 73a/73b preferably each have a resistance value of 32×R. In such a circuit intended for use with molten aluminum or aluminum alloys, the R value may be 0.020 ohm with the resistances of the various resistors thus being:

23a/23b=0.020 ohm
33a/33b=4×0.15 ohm in parallel=0.0375 ohm
43a/43b=2×0.15 ohm in parallel=0.075 ohm
53a/53b=0.15 ohm
63a/63b=0.33 ohm; and
73a/73b=2×0.33 ohm in series=0.66 ohm.

In an exemplary control sequence, resistors 23a/23b are turned on first. Then, as the voltage decays, additional resistors are turned on as needed according to a binary coded sequence starting with resistors 73a/73b which produces the smallest current change. Then resistors 73a/73b are turned off and resistors 63a/63b are turned on causing twice the current change that resistors 73a/73b did. Then both resistors 73a/73b and 63a/63b are turned on, and so forth in a binary sequence, i.e. 100000, 100001, 100010, 100011, 100100, 100101, 100110, . . . 111111 (i.e. 32 states in all), where the least significant digit controls resistors 73a/73b and the most significant digit controls resistors 23a/23b. This sequence of 32 resistor transitions are brought successively into use as the current drops to around 60 amps to maintain the measurement current within the desired range. In fact, only some of the 32 states 100001 to 111111 may be effective to maintain the current value, and normally at least 5 or 6 states are effective. By switching to these states, the current flow through the metal in the passage 14 can be kept within a desired range of e.g. 60 to 65 amps during the time required for a measurement of metal cleanliness (usually at least 30 seconds) despite the rapid voltage decay of the ultra-capacitors 11a and 11b.

While in FIG. 1 each circuit leg is provided with a single FET to enable the circuit leg to be switched in or switched out of the circuit, it is alternatively possible to provide two or more parallel-connected FETs in each circuit leg. The FETs of such an arrangement would all be switched on or switched off at the same time. The advantage of such an arrangement is that multiple FETs connected in parallel would further reduce any resistance values introduced by the individual FETs to further minimize heat losses in the circuitry. For example, in one embodiment it is desirable to keep the FET resistance below about 1 milli-ohm. This could be done, for example, by using a single FET having a resistance value of 0.8 milli-ohm when in the ON condition, or by using say 10 FETs in parallel, each with a resistance value of 8.0 milli-ohm. Thus, FETs or larger resistance values may still be employed. Of course, 10 FETs have a larger footprint than a single FET that may make them more susceptible to noise pick-up, so it is advisable to use FETs of smaller resistance values when they are available. By keeping the voltage of the ultra-capacitors low and the FET resistance low in the circuit legs, unwanted heat generation can be kept to a minimum, thereby making it possible to design measuring equipment having no need for heavy and bulky heat sinks, thus minimizing equipment size and weight and minimizing susceptibility of the equipment to pick-up external and internal electrical noise, thereby keeping the voltage signal "clean." If considered advantageous for particular applications, however, FETs 23a and 23b alone may be provided with heat sinks since they take the majority of the current flow and are in the ON condition all of the time during the measurement.

The activation of the various resistors in the two resistor ladder circuits can be in response to automatic monitoring of the current in real time via transducer 17 with appropriate generation of alerts to the FET controller 18. Suitable components to generate such alerts may be associated with the current meter A. An alternative approach is to pre-program the necessary operations into the FET controller 18 before a measurement operation is commenced so that the adjustments are made automatically according to an optimal time/resistance program established in advance for the circuit and the metal to be measured. Different metals may of course require different programs in view of their different resistance values and current flow characteristics.

To predetermine the sequence used to switch resistors on and off in the ladder for a particular metal, a calibration routine may be performed before actual measurement commences. According to such a routine, the ultra-capacitors 11a/11b are charged to a voltage that would provide greater than 65 amps when resistors 23a/23b are first turned on. This initial current may be around 70-80 amps. Then, resistors 23a/23b are turned on and, when the current decreases to about 65 amps, the voltage of the ultra-capacitors 11a, 11b is recorded and is used to determine the ultra-capacitor charge voltage. When the current decreases to 60 amps, the remaining resistors are turned on in a binary coded sequence as indicated above until a current of 65 amps is once again established. The resistor binary state and ultra-cap voltage are recorded within controller 18 for the first transition. Each time the current decreases to 60 amps, the remaining resistors are turned on in the binary coded sequence until 65 amps is again achieved and the next transition binary state and ultra-cap voltage are recorded. This is done until all resistors in the ladders have been turned on and the current falls below 60 amps indicating the calibration is complete. During sampling, each effective transition state is set and recorded as stored calibration transition states. The recorded data from the calibration routine is employed by the controller 18 during a cleanliness measurement operation to issue the voltage signals via lines 20 to 70 to control the FETs to maintain the measurement current within the desired range. A time/resistance calibration operation may be carried out for each different molten metal, or before every measurement if desired.

While the FETs are capable of switching their respective circuit legs on or off very rapidly, e.g. in a matter of micro-seconds, employing the binary sequence of operation as described, it is possible to discard any voltage measurements collected by voltage recorder V for the duration of the switching event as there will inevitable be a voltage jump when additional resistor(s) switch in or out and this may confuse the significance of the signal at that particular time. Thus, the voltage recorder V may be programmed, e.g. by a further micro-processor located within recorder V on an analog board (not shown), to automatically stop registering or recording of the voltage signal during a switching event as prompted by signals from the controller 18. Alternatively, the results from such switching periods, although recorded by recorder V, may simply be ignored by software during analysis of the voltage signal.

The voltage output recorded during a measurement period may be processed and analyzed to determine the number and characteristics of inclusions in the same manner as for conventional LiMCA devices, and the apparatus may be provided with a suitable analyzer for analyzing the voltage signal and this may be incorporated into, or associated with, element V shown in the drawings. However, it is advantageous to analyze the signal in the manner described below as described with reference to FIGS. 3A-8, and to provide the analyzer of the LiMCA device with a computer-readable non-transitory storage medium storing statements and instructions which, when executed by one or more processors, cause the processors to analyze the signal in the manner described with reference to FIGS. 3A-8.

The features of the exemplary embodiments of the present application enable the device to avoid much external and internal electrical interference, so the resulting signal may be analyzed without the need for additional apparatus (e.g. further electrodes) or routines that may be required in the prior art, such as the Marcotte et al. patent mentioned above. The exemplary embodiments may thus employ only two electrodes, i.e. electrodes 12*a* and 12*b* as shown. It is additionally useful to provide the exemplary embodiments with the ability to condition or purge the LiMCA probe prior to carrying out a measurement or auto calibration routine. This is done by delivering a very high current (e.g. 300 A or more) through the passage to displace or eliminate inclusions trapped in the passage or scale etc. lining the sides. This can be done by discharging the ultra-capacitors 11*a*, 11*b* directly through the molten metal in the passage via a circuit having little or no electrical resistance, e.g. containing no ballast resistors. For this purpose, the ultra-capacitors may be connected in parallel (which is normal) or in series (when a higher current is required). Referring again to FIG. 1, these operations are controlled by FETs 25, 80, 90 and 100. With all other FETs turned off, turning on FETs 25, 80 and 90 causes the ultra-capacitors 11*a*, 11*b* to discharge in parallel through the electrode 12*a*. On the other hand, turning on FETs 80 and 100 with FET 25 turned off causes the ultra-capacitors to discharge in series. Control of these discharge FETs is maintained by voltages applied through lines 24, 26, 27 and 28 according to signals from controller 18. Line 24 controls FET 25, line 26 controls FET 80, line 27 controls FET 90, and line 28 controls FET 100. The current value during these discharges is determined by the resistance value of the metal between the electrodes plus current path impedances. The discharge can be selected with a duration lasting, for example, from 5 ms to 995 ms as required.

Figure 2:
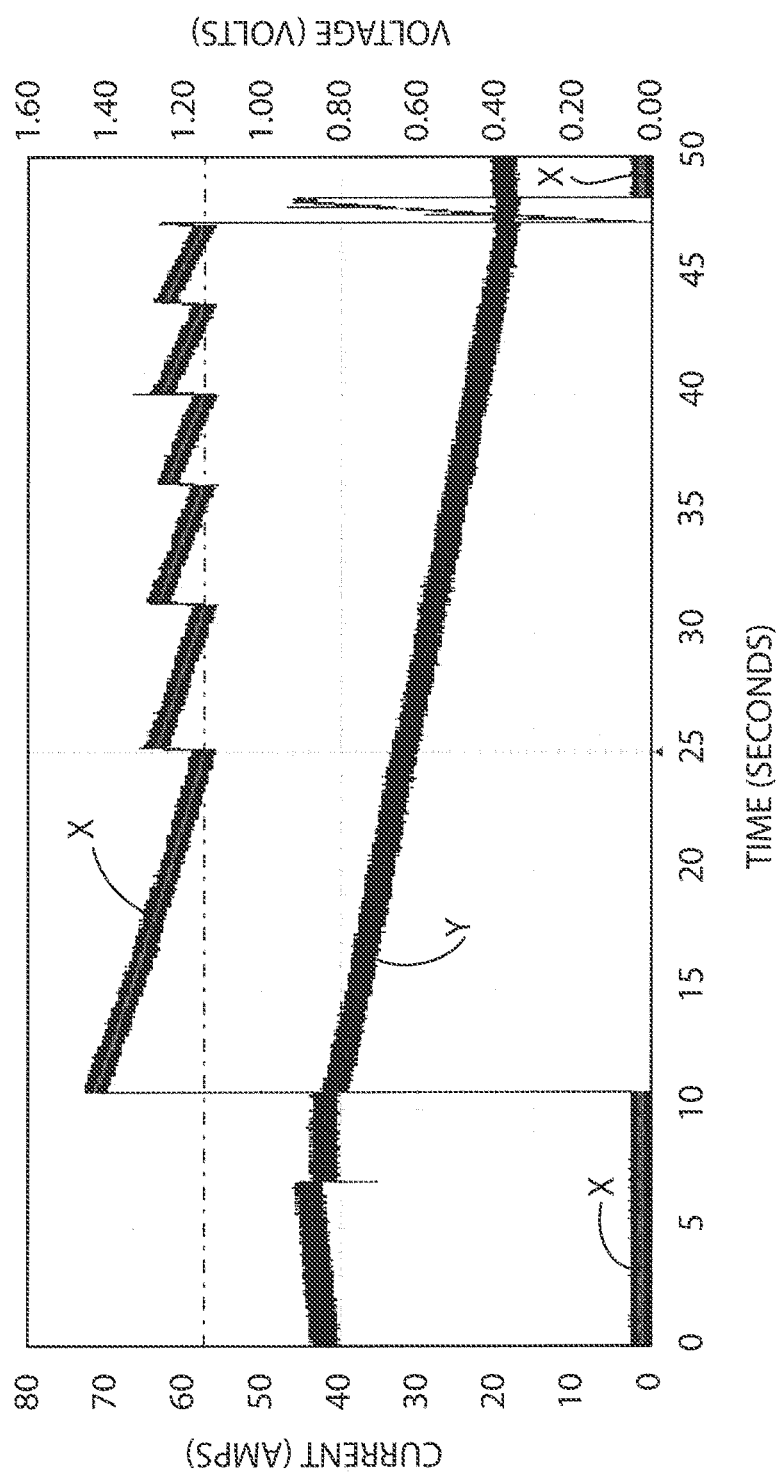
FIG. 2 is a chart showing the results of a test carried out according to an exemplary embodiment of the invention.

Apparatus of the above kind has been subjected to tests under real conditions in liquid aluminum in kilns at several test locations. Data saved during these tests included resistor states, discharge current, capacitor voltage, time, and many other parameters. The results of one of such tests are shown in FIG. 2 of the accompanying drawings, in which waveform X shows the measuring current in amps passing between the electrodes during the test period, and waveform Y shows the ultra-capacitor voltage as it discharges during the test period. It can be seen that, despite the decay of the discharge voltage of the ultra-capacitors, the current between the electrodes was maintained in the range of 58 to 63 amps.

FIGS. 3A-C and 4-8 illustrate flow charts, system diagrams, and sample graphs of a method 300 according to embodiments of the present invention to filter noise and to qualify inclusions in molten metal. As previously described, as current flows through the molten metal, voltage across the electrodes 12*a* and 12*b* is measured by voltage recording and analyzing apparatus V so that the presence and characteristics of pulses in the voltage trace characteristic of metal inclusions can be assessed using the method 300.

In general, the method 300 provides continuous filtering in real time to identify and remove both low and high level noise by tracking running averages and creating thresholds, slopes and boundaries of a digitized analog signal (i.e., as provided by the voltage recording and analyzing apparatus V of FIG. 1). A signal produced by an inclusion passing through the narrow passageway 14 to the interior of the probe 13 has a series of parameters including defined shape, rise time, fall time, width and amplitude. The method 300 measures these parameters and determines if the signal represents a valid inclusion. The method 300 is adaptive in terms of noise and inclusion size such that the allowable level of noise increases as the size of the inclusion increases. This adaptive feature permits the measurement of larger inclusions in a higher noise environment while keeping the signal to noise ratio high.

Figure 3A:
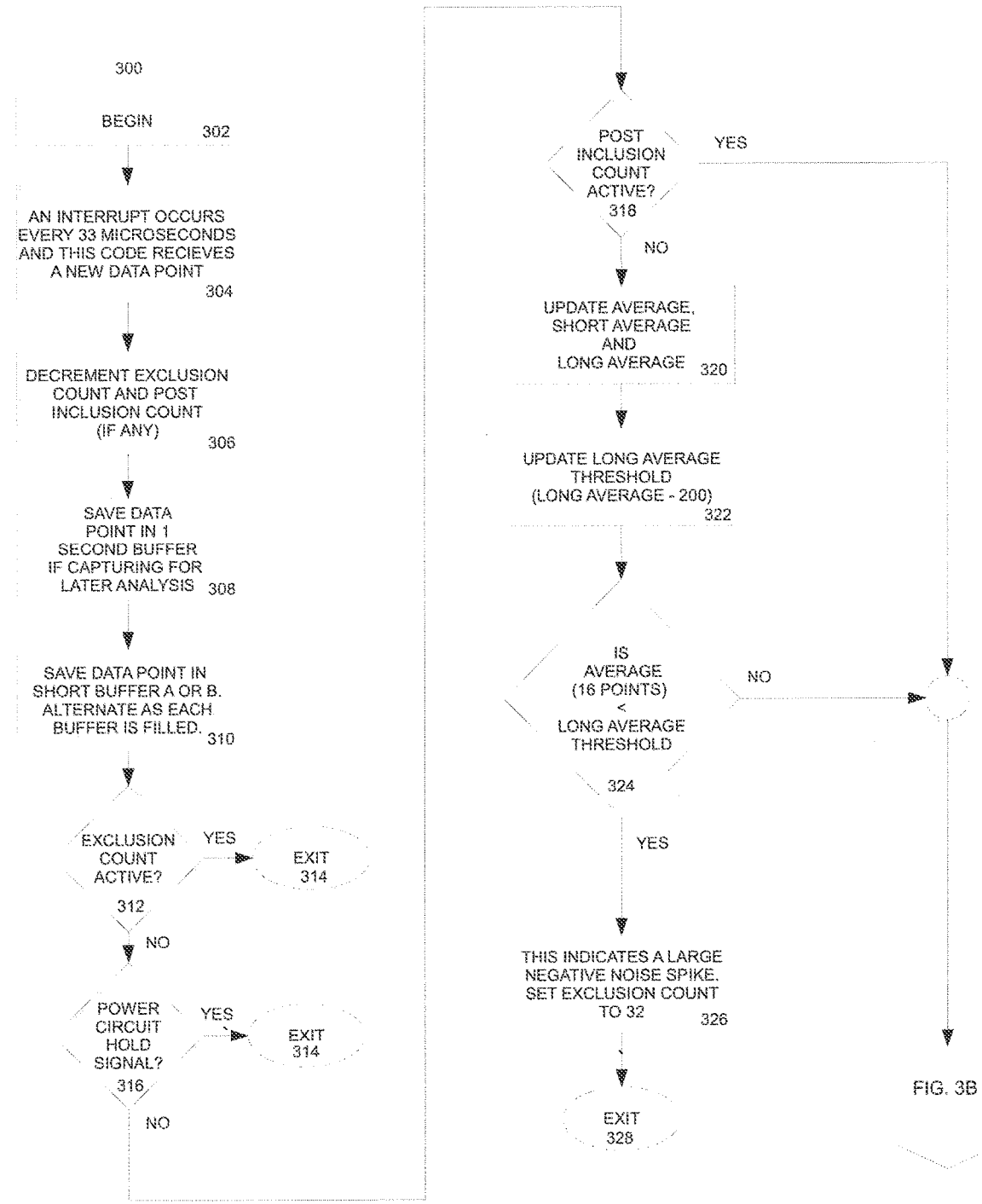

Details of the exemplary method 300 begin at step 302 of FIG. 3A. A new data point is received from the voltage recording and analyzing apparatus V (of FIG. 1) at step 304 caused by an interrupt that occurs at regular intervals (e.g., every 33 microseconds). An exclusion count variable and a post inclusion count variable are each decremented by one at step 306. A data point is saved in a one second buffer variable (capable of retaining, for example, up to 30,000 data points) at step 308 when data is being captured for later analysis. The data point is also saved in a short buffer variable (A or B) at step 310. The storage in each of the short buffer variables A and B (each capable of retaining, for example, up to 256 data points) is alternated as each buffer is filled.

If the exclusion count variable is active, having a value not equal to zero, as determined at step 312 then the method 300 exits at step 314. If the exclusion count variable is not active, having a value equal to zero, then the method 300 continues to step 316 to determine if a power circuit hold signal exists.

If a hold signal exists, then method 300 may exit at step 314. A hold signal may be generated, for instance, by a power module. The power module generates the hold signal a short period of time (e.g., 1 millisecond) before changing resistors. The power module then releases the hold signal 1 millisecond after changing resistors. This prevents the current change that occurs in conjunction with the resistor change from being interpreted as an inclusion.

If no hold signal exists, then the method 300 continues to step 318 to determine if the post inclusion count variable is active. If the post inclusion count variable is active, then the method 300 continues to FIG. 3B. If the post inclusion count variable is not active, then the method 300 continues to step 320 to update a plurality of averaging variables: an average variable (defined, for instance, as sixteen samples beginning four samples back), a short average variable (defined, for instance, as eight samples beginning four samples back) and a long average variable (defined, for instance, as 256 samples). A long average threshold variable is updated at step 322 by subtracting 200 units from the long average variable updated at step 320. At step 324, it is determined if the average variable (as updated at step 320) is less than the long average threshold variable, as updated at step 322. A positive determination at step 324 is an indication of a large negative noise spike, and the exclusion count variable is set to thirty-two and the method 300 exits at step 328. The method 300 continues to FIG. 3B when the determination step 324 is negative (i.e., there is not a large noise spike).

The method 300 functions in one of three operating state: state zero tracks the noise level of data and a baseline average level while waiting for an inclusion; state one is when the inclusion is in a sensing zone and state two is when the inclusion has left the sensing zone.

Referring to FIG. 3B, if the operating state is zero, as determined at step 340 because the noise level of data is at a baseline average level, then processing enters a state zero enter process 400 in FIG. 4. If the operating state is not equal to zero, as determined at step 340, then the method 300 continues to step 342 to determine if the current data point is less than a down threshold variable that may be simply the up threshold, which is 225. If the determination at step 342 is negative processing continues to FIG. 3C. A positive determination at step 342 could represent the end of an inclusion 344 passing the passageway (orifice) 14 of the system 10 (see FIG. 1). An inclusion count variable is then set to the peak value less the base count at step 346. The peak value is less the base count at step 346. Each sample/data point measured after the up threshold is crossed, and before the down threshold is crossed, is evaluated to see if it is the largest value encountered in this inclusion, and the largest such value is the peak value. After the down threshold is crossed, the baseline is subtracted from the peak value to determine the height. A lookup table (i.e., a count-to-micron table) is referenced to determine the inclusion size at step 348. Minimum and maximum acceptable widths for the inclusion (determined at step 348) are determined using min/max width lookup tables as step 350. A maximum acceptable baseline noise for the inclusion size (determined at step 348) is determined using a maximum noise lookup table at step 352.

If the minimum width of the inclusion is less than a sample count and the sample count variable is less than the maximum width of the inclusion, as determined at step 354, then processing continues to step 356. The sample count variable is set to 0 when the up threshold is crossed. It is incremented by one for every data point sampled until the down threshold is crossed. It is directly proportional to the width of the inclusion pulse. The sample width is compared to two lookup tables, one of maximum widths for each inclusion size, and one of minimum widths for each inclusion size. A negative determination at step 354 means that the inclusion was too wide or too narrow 358 (i.e., not a valid inclusion) and the operating state of the method 300 is set to zero at step 360. A valid inclusion is assessed 362 when a delta variable is less than a maximum acceptable noise level as determined at step 356. The delta variable is calculated by subtracting the minimum value in the data points which were used to compute the baseline level from the maximum value in the data points used to calculate the baseline level. It indicates the noise level in the baseline signal. For each inclusion size, there is a maximum delta value which will be accepted. In practice, it says that for larger inclusions, more baseline noise will be tolerated, but for smaller inclusions a low level of baseline noise will is required. It qualifies the signal to noise ratio of the data. The operating state of the method 300 is then set to two at step 364. Baseline noise is considered too high 366 (i.e., not a valid inclusion) when the delta variable is equal to or greater than the maximum acceptable noise as determined at step 356. In this case, the operating state of the method 300 is set to zero at step 360.

An additional filter may be used to measure the width of the base of the inclusion (below down threshold). This is compared to the width counted from when the up threshold is crossed. The difference between the two of these corresponds to the slope of the leading edge of the inclusion. This enables qualification of signals as either inclusions or gas bubbles.

Referring to FIG. 3C, if all the following conditions are true, then the method 300 continues to a set state one process 500 in FIG. 5A:
 (a) the operating state is not equal to zero as determined at step 370;
 (b) the current data point is greater than the up threshold variable as determined at step 372;
 (c) the delta variable is less than 500 as determined at step 374;
 (d) a persistent delta variable is less than 1000 as determined at step 376; and
 (e) the average variable is greater than the long average threshold variable as determined at step 378.

If any one of the above conditions (a) to (e) is false, then processing continues to determine if method 300 is in operating state one at step 380 or in operating state two at step 382. If the method 300 is in operating state one, as determined in step 380, then processing continues to a state one process 520 in FIG. 5B. If the method 300 is in operating state two, as determined in step 382, then processing continues to a state two process 600 in FIG. 6. If the method 300 is not in operating state one or two then the method 300 ends at step 384.

FIG. 4 illustrates a state zero enter process 400 that is initiated when the operating state is assessed at state zero at step 340 (FIG. 3B). The maximum and minimum (max/min) values of ten data points beginning four samples back are calculated at step 402. The difference between the max/min values are calculated as step 404. The difference calculated at step 404 represents the immediate noise level and is saved as the delta variable. The persistent delta variable is set from the delta variable at step 406 when the post inclusion count variable is active as determined at step 408. The max/min values of twenty eight data points beginning four samples back are calculated at step 410 when the post inclusion count variable is not active as determined at step 408. The difference between the max/min values (from step 410) is calculated at step 412. The difference calculated at step 412 represents the immediate noise level and is saved as the persistent delta variable.

After either step 406 or 412 (depending on result of step 408), processing continues to step 414 to calculate the up threshold variable as the short average plus 350 The default threshold height may be set at 350, but can be dynamically changed from the PC controlling the Nomad at any time. It permits adjustment to tailor the filter to the data. The result of this calculation corresponds to the minimum height accepted as the start of an inclusion. At step 416, the down threshold variable is calculated as the up threshold variable less 225 This value was empirically arrived at empirically. It provides for a 125 count hysteresis between up and down threshold, which prevents noise from terminating inclusion detection prematurely. A large range of values other than 225 could be used. The result of this calculation corresponds to the height that marks the end of an inclusion. The state zero process 400 is now complete.

FIG. 5A illustrates a set state one process 500 that is initiated when all conditions 370, 372, 374, 376, and 378 are satisfied as per FIG. 3C. Initiation of process 500 means a potential start of an inclusion so the sample count variable is set to one at step 502. A peak variable is set to the value of the current data point at step 504 and the baseline is set to the average variable as step 506. A saved delta variable is set to the delta variable at step 508 and the method 300 operating state is set to one at step 510.

FIG. 5B illustrates a state one process 520 initiated when the method 300 is determined to be in operating state one at step 380 as per FIG. 3C. When the current data point is greater than the down threshold variable, as determined at step 522, and the current data point is greater than the peak variable, as determined at step 524, then the peak variable is set to the current data point at step 526. Step 526 is skipped when the determination of step 524 is false. The state one process 520 exits when the determination at step 522 is false. The sample count variable is incremented at step 528. If the sample count is greater than 50, as determined at step 530, then the method 300 operating state is set to zero at step 532. In this embodiment the widest signal accepted for an inclusion is 40 counts, with the result that any width over 40 would be invalid and ignored. The value of 50 aborts detection without waiting for the end of an inclusion, because at 50 (or any value over 40) the signal is invalid and will be recognized as an inclusion. Other sample count numbers could be used. In this embodiment, if the sample count is equal to or less than fifty, as determined at step 530, then the state one process 520 exits.

Figure 6:
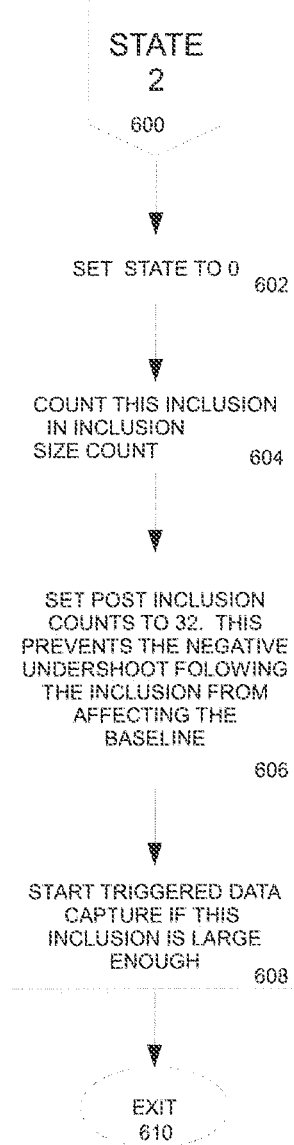
FIG. 6 is a flow chart illustrating a further operating state according to an exemplary embodiment of the present invention.

FIG. 6 illustrates a state two process 600 to mark the end of an inclusion that is initiated when the method 300 is determined to be in operating state two at step 382 as per FIG. 3C. The method 300 operating state is set to zero at step 602. The inclusion is counted in the appropriate inclusion size count at step 604. The post inclusion count variable is set to thirty two at step 606 to prevent the negative undershoot following the inclusion from affecting the baseline. Thirty two gives the system a 1 millisecond delay after the end of an inclusion to allow the signal to recover a stable baseline before looking for inclusions. This allows the undershoot that occurs after the inclusion passes through the orifice to be ignored. A wide ranges of alternatives to 1 millisecond could be used. It was chosen as a workable value based on sample data. Triggered data capture is started at step 608 when the inclusion is sufficiently large (as specified by the system operator), and the process 600 exits at step 610.

Figure 7:
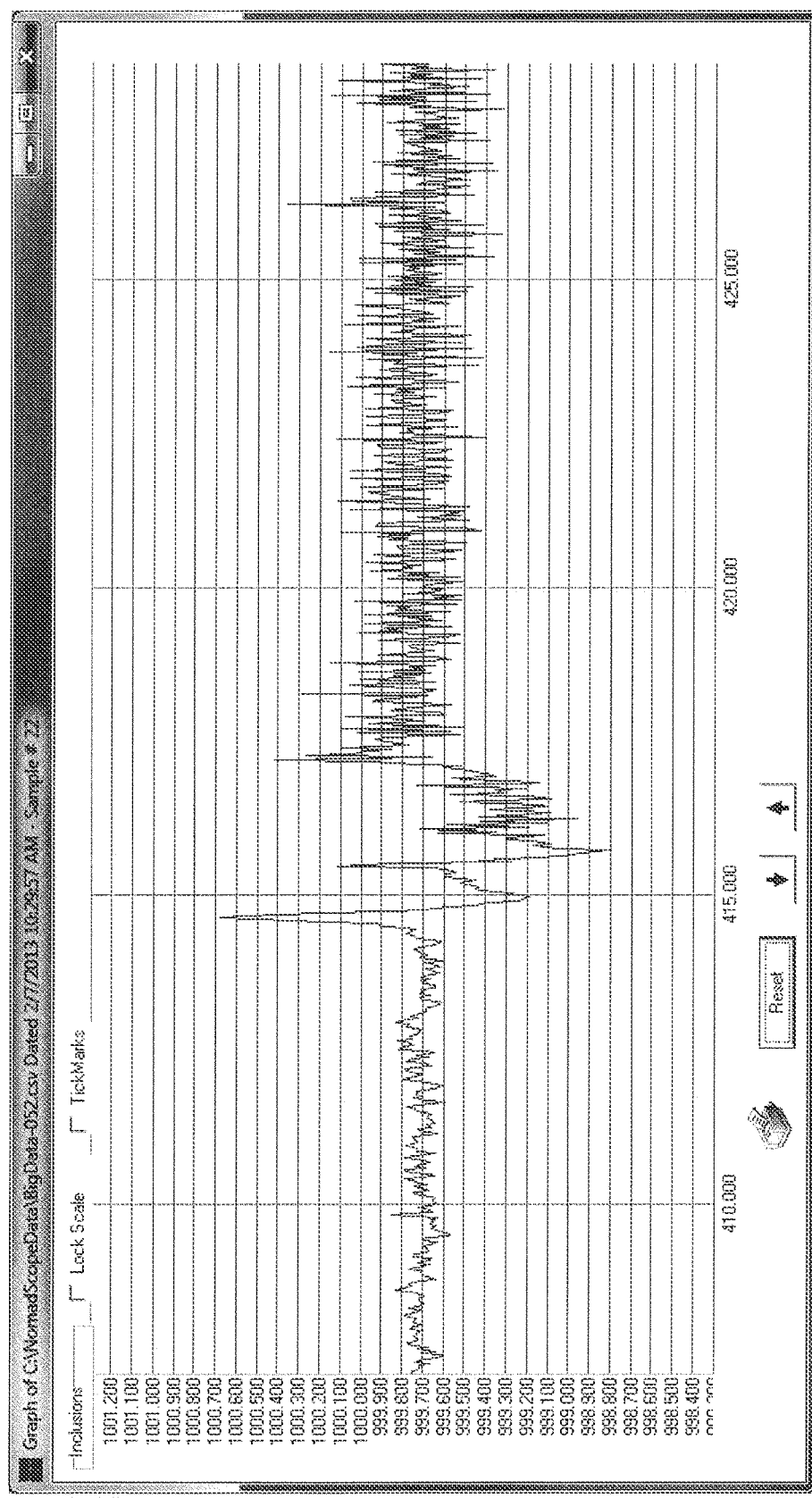

FIG. 7 provides an example graph showing a valid inclusion signal and interfering noise. In FIG. 7, a valid inclusion is at time 414.5 s. All of the remaining noise was rejected by the method 300. As described above, the method 300 is performed continuously to identify inclusion parameters using running averages, thresholds, slope and boundaries. Since the analysis is performed in real time, at any point in which the signal does not fall within the parameter criteria the search simply continues. If all parameter criteria are met for identifying an inclusion, it is marked and categorized. Unwanted noise is ignored. Both low noise level (<201 μm) and high level noise (>250 μm) such as induced transients and periodic noise are effectively ignored. The method 300 provides the noise rejection necessary to operate effectively with two probes 12a and 12b without using traditional digital signal processing techniques.

The methods, processes and techniques described herein can be implemented by one or more special-purpose computing devices and may also be implemented using general purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 8:
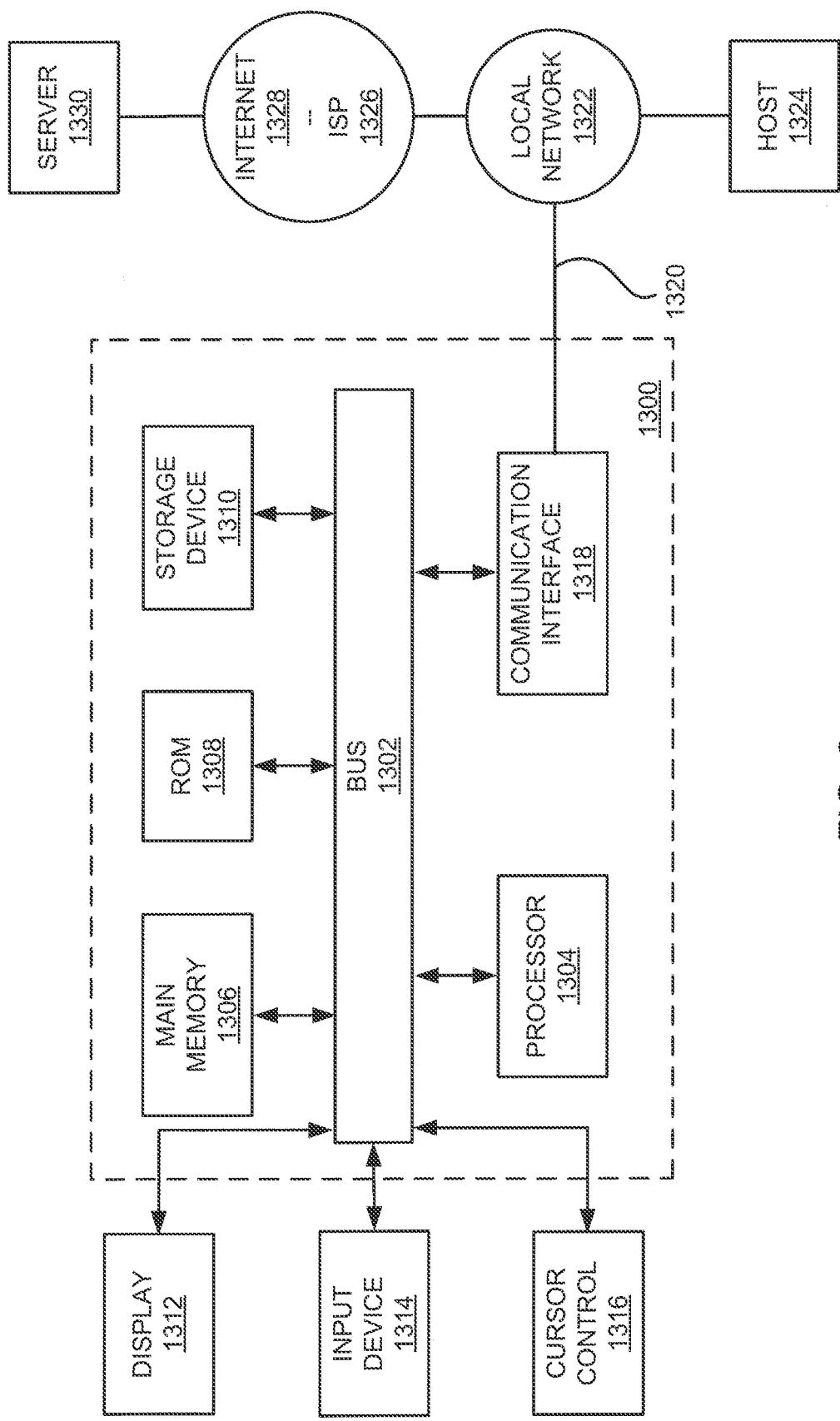
FIG. 8 illustrates a computer system upon which the various embodiments may be implemented.

For example, referring to FIG. 8, a computer system 1300 includes a bus 1302 or other communication mechanism for communicating information, and a hardware processor 1304 coupled with the bus for processing information. The hardware processor 1304 may be, for example, a general purpose microprocessor.

The computer system 1300 also typically includes a memory 1306, such as a random access memory (RAM) or other dynamic storage device, coupled to the bus for storing information and instructions to be executed by processor. The memory 1306 also may be used for storing temporary variables or other intermediate information during execution of instructions to be executed by the processor. Such instructions, when stored in non-transitory storage media accessible to processor 1304, render the computer system into a special-purpose machine that is customized to perform the operations specified in the instructions.

The computer system 1300 further includes a read only memory (ROM) 1308 or other static storage device coupled to the bus for storing static information and instructions for the processor. A storage device 1310, such as a magnetic disk or optical disk, can also be provided and coupled to the bus for storing information and instructions.

The computer system 1300 may be coupled via the bus 1302 to a display 1312 (CRT, LCD, etc.), for displaying information to a computer user. An input device 1314, including alphanumeric and other keys, is coupled to bus for communicating information and command selections to the processor. Another type of user input device is cursor control, such as a mouse, a trackball, or cursor direction keys for communicating direction information and command selections to the processor and for controlling cursor movement on display. This input device typically has two degrees of freedom in two axes, a first axis (e.g., x) and a second axis (e.g., y), that allows the device to specify positions in a plane.

The computer system 1300 may implement the techniques described herein using customized hard-wired logic, one or more ASICs or FPGAs, firmware and/or program logic which in combination with the computer system causes or programs computer system to be a special purpose machine. According to one embodiment, the techniques herein are performed by the computer system 1300 in response to the processor 1304 executing one or more sequences of one or more instructions contained in the memory 1306. Such instructions may be read into the memory 1306 from another storage medium, such as a storage device 1310. Execution of the sequences of instructions contained in the memory 1306 causes the processor 1304 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device. Volatile media includes dynamic memory, such as main memory. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise the bus. Transmission media can also take the form of acoustic or light waves, such as those generated during radio-wave and infra-red data communications.

Various forms of media may be involved in carrying one or more sequences of one or more instructions to the processor for execution. For example, the instructions may initially be carried on a magnetic disk or solid state drive of a remote computer. The remote computer can load the instructions into its dynamic memory and send the instructions over a telephone line using a modem. The modem local to the computer system 1300 can receive the data on the telephone line and use an infra-red transmitter to convert the data to an infra-red signal. An infra-red detector can receive the data carried in the infra-red signal and appropriate circuitry can place the data on the bus 1302. The bus 1302 carries the data to the main memory 1306, from which the processor 1304 retrieves and executes the instructions. The instructions received by main memory 1306 may optionally be stored on the storage device 1310 either before or after execution by the processor 1304.

The computer system 1300 can also include a communication interface 1318 coupled to the bus 1302. The communication interface 1318 provides a two-way data communication coupling to a network link 1320 that is connected to a local network 1322. For example, the communication interface may be an integrated services digital network (ISDN) card, cable modem, satellite modem, or a modem to provide a data communication connection to a corresponding type of telephone line. As another example, the communication interface may be a local area network (LAN) card to provide a data communication connection to a compatible LAN. Wireless links may also be implemented. In any such implementation, the communication interface sends and receives electrical, electromagnetic or optical signals that carry digital data streams representing various types of information.

The network link 1320 typically provides data communication through one or more networks to other data devices. For example, the network link 1320 may provide a connection through the local network to a host computer or to data equipment operated by an Internet Service Provider (ISP) 1326. The ISP in turn provides data communication services through the world wide packet data communication network now commonly referred to as the Internet 1328. The local network 1322 and Internet 1328 both use electrical, electromagnetic or optical signals that carry digital data streams. The signals through the various networks and the signals on the network link 1320 and through the communication interface 1318, which carry the digital data to and from the computer system 1300, are example forms of transmission media.

The computer system 1300 can send messages and receive data, including program code, through the network(s), the network link 1320 and communication interface 1318. In the Internet 1328 example, a server 1330 might transmit a requested code for an application program through the Internet 1328, the ISP 1326, the local network 1322 and the communication interface 1318. The received code may be executed by the processor 1304 as it is received, and/or stored in the storage device 1310, or other non-volatile storage for later execution.

This detailed description of the apparatus is used to illustrate exemplary embodiments of the system and the method of the present invention. It will be clear to those skilled in the art that various modifications can be made in the present apparatus of the system and that various alternative embodiments can be utilized. Therefore, it will be recognized that various modifications can be made in both the method and apparatus of the present invention and in the applications to which the method and system are applied without departing from the scope of the invention, which is limited only by the appended claims.

What is claimed is:

1. A method comprising:

charging at least one ultra-capacitor coupled to electrodes partially immersed in a molten metal and positioned on opposite sides of a wall made of electrically resistive material;

discharging the at least one ultra-capacitor through molten metal advancing through a passage in the wall between the electrodes, wherein discharging the at least one ultra-capacitor includes maintaining a measurement current within a pre-determined current range at least for a time required for measurement of cleanliness of the molten metal;

measuring a voltage across the electrodes during discharging of the at least one ultra-capacitor, wherein measuring the voltage occurs as the molten metal advances through the passage;

sampling digital data of the measured voltage across the electrodes to generate data samples representative of the molten metal advancing through the passage;

updating a delayed running average of the data samples to establish a baseline for identifying sudden changes in amplitude of the data samples, wherein the delayed running average is associated with quantities of molten metal recently advanced through the passage;

determining a threshold by adding a prescribed value to the baseline;

identifying a possible inclusion when a significant number of data samples exceeds the threshold;

identifying an end of the possible inclusion when a prescribed number of data samples fall below the threshold after identifying the possible inclusion;

bypassing a preset number of data samples when the end of the possible inclusion is identified, wherein bypassing the preset number of data samples includes not updating the delayed running average with the preset number of data samples; and comparing a parameter of the possible inclusion with a lookup table to categorize the possible inclusion as either (i) an actual inclusion or (ii) noise.

2. The method of claim 1, wherein the parameter includes width.

3. The method of claim 2, wherein charging the at least one ultra-capacitor includes charging the at least one ultra-capacitor to a voltage of 2.7 volts or less;
   wherein discharging the at least one ultra-capacitor includes discharging the at least one ultra-capacitor, via a resistor ladder network circuit associated with each of the at least one ultra-capacitors, through the molten metal advancing through the passage between an interior electrode positioned in the interior of a probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps through the molten metal advancing through the passage; and
   switching the field effect transistors of the circuit legs of each resistor ladder network circuit between the non-conductive OFF condition and the fully conductive ON condition according to a sequence for maintaining the measurement current within the pre-determined current range; and
   wherein measuring the voltage across the electrodes is performed across internal and external electrodes.

4. The method of claim 1, further comprising saving data points of the actual inclusion when categorized by comparing the parameter.

5. The method of claim 4, wherein charging the at least one ultra-capacitor includes charging the at least one ultra-capacitor to a voltage of 2.7 volts or less;
   wherein discharging the at least one ultra-capacitor includes discharging the at least one ultra-capacitor, via a resistor ladder network circuit associated with each of the at least one ultra-capacitors, through the molten metal advancing through the passage between an interior electrode positioned in the interior of a probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps through the molten metal advancing through the passage; and
   switching the field effect transistors of the circuit legs of each resistor ladder network circuit between the non-conductive OFF condition and the fully conductive ON condition according to a sequence for maintaining the measurement current within the pre-determined current range; and
   wherein measuring the voltage across the electrodes is performed across internal and external electrodes.

6. The method of claim 1, further comprising monitoring a noise level present in the baseline.

7. The method of claim 6, further comprising evaluating the noise level in the baseline preceding the possible inclusion after identifying the possible inclusion.

8. The method of claim 7, wherein charging the at least one ultra-capacitor includes charging the at least one ultra-capacitor to a voltage of 2.7 volts or less;
   wherein discharging the at least one ultra-capacitor includes discharging the at least one ultra-capacitor, via a resistor ladder network circuit associated with each of the at least one ultra-capacitors, through the molten metal advancing through the passage between an interior electrode positioned in the interior of a probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps through the molten metal advancing through the passage; and
   switching the field effect transistors of the circuit legs of each resistor ladder network circuit between the non-conductive OFF condition and the fully conductive ON condition according to a sequence for maintaining the measurement current within the pre-determined current range; and
   wherein measuring the voltage across the electrodes is performed across internal and external electrodes.

9. The method of claim 6, further comprising dynamically adjusting a maximum acceptable noise level based on a width of the actual inclusion.

10. The method of claim 9, wherein charging the at least one ultra-capacitor includes charging the at least one ultra-capacitor to a voltage of 2.7 volts or less;
    wherein discharging the at least one ultra-capacitor includes discharging the at least one ultra-capacitor, via a resistor ladder network circuit associated with each of the at least one ultra-capacitors, through the molten metal advancing through the passage between an interior electrode positioned in the interior of a probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps through the molten metal advancing through the passage; and
    switching the field effect transistors of the circuit legs of each resistor ladder network circuit between the non-conductive OFF condition and the fully conductive ON condition according to a sequence for maintaining the measurement current within the pre-determined current range; and
    wherein measuring the voltage across the electrodes is performed across internal and external electrodes.

11. The method of claim 6, wherein charging the at least one ultra-capacitor includes charging the at least one ultra-capacitor to a voltage of 2.7 volts or less;
    wherein discharging the at least one ultra-capacitor includes discharging the at least one ultra-capacitor, via a resistor ladder network circuit associated with each of the at least one ultra-capacitors, through the molten metal advancing through the passage between an interior electrode positioned in the interior of a probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps through the molten metal advancing through the passage; and switching the field effect transistors of the circuit legs of each resistor ladder network circuit between the non-conductive OFF condition and the fully conductive ON condition according to a sequence for maintaining the measurement current within the pre-determined current range; and wherein measuring the voltage across the electrodes is performed across internal and external electrodes.

12. The method of claim 1, wherein charging the at least one ultra-capacitor includes charging the at least one ultra-capacitor to a voltage of 2.7 volts or less;

wherein discharging the at least one ultra-capacitor includes discharging the at least one ultra-capacitor, via a resistor ladder network circuit associated with each of the at least one ultra-capacitors, through the molten metal advancing through the passage between an interior electrode positioned in the interior of a probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps through the molten metal advancing through the passage; and switching the field effect transistors of the circuit legs of each resistor ladder network circuit between the non-conductive OFF condition and the fully conductive ON condition according to a sequence for maintaining the measurement current within the pre-determined current range; and wherein measuring the voltage across the electrodes is performed across the internal and external electrodes.

13. The method of claim 1, wherein the pre-determined current range is between 55 amps and 100 amps.

14. A computer-readable non-transitory storage medium storing statements and instructions, which, when executed by one or more processors, cause the one or more processors to:

charge at least one ultra-capacitor coupled to electrodes partially immersed in a molten metal and positioned on opposite sides of a wall made of electrically resistive material;

discharge the at least one ultra-capacitor through molten metal advancing through a passage in the wall between the electrodes, wherein discharging the at least one ultra-capacitor includes maintaining a measurement current within a pre-determined current range at least for a time required for measurement of cleanliness of the molten metal;

measure a voltage across the electrodes during discharging of the at least one ultra-capacitor, wherein measuring the voltage occurs as the molten metal advances through the passage;

sample digital data of the measured voltage across the electrodes to generate data samples representative of the molten metal advancing through the passage;

update a delayed running average of the data samples to establish a baseline for identifying sudden changes in amplitude of the data samples, wherein the delayed running average is associated with quantities of molten metal recently advanced through the passage;

determine a threshold by adding a prescribed value to the baseline;

identify a possible inclusion when a significant number of data samples exceeds the threshold;

identify an end of the possible inclusion when a prescribed number of data samples fall below the threshold after identifying the possible inclusion;

bypass a preset number of data samples when the end of the possible inclusion is identified, wherein bypassing the preset number of data samples includes not updating the delayed running average with the preset number of data samples; and compare a parameter of the possible inclusion with a lookup table to categorize the possible inclusion as either (i) an actual inclusion or (ii) noise.

15. The medium of claim 14, wherein the parameter includes width.

16. The medium of claim 14, wherein the statements and instructions, which, when executed by the one or more processors, cause the one or more processors to save data points of the actual inclusion when categorized when comparing the parameter.

17. The medium of claim 14, to further monitor a noise level present in the baseline.

18. The medium of claim 17, to further evaluate the noise level in the baseline preceding the possible inclusion after identifying the possible inclusion.

19. The medium of claim 17, further comprising dynamically adjusting a maximum acceptable noise level based on a width of the actual inclusion.

20. Apparatus for measuring cleanliness of a molten metal, the apparatus comprising:

one or more rechargeable ultra-capacitors operable at a discharge voltage of 2.7 volts or less;

at least two electrodes;

a metal cleanliness probe having an interior, a wall made of electrically resistive material and a passage in the wall interconnecting the interior with an exterior of the probe to allow molten metal to pass therethrough, wherein one of the at least two electrodes is positioned in the interior of the probe as an interior electrode and another of the at least two electrodes is positioned outside the probe as an exterior electrode;

a device measuring voltage across the interior and exterior electrodes and generating a voltage signal;

for for each of the one or more ultra-capacitors, an associated resistor ladder network circuit interconnecting its associated ultra-capacitor with one of the electrodes, each resistor ladder network circuit comprising two or more resistors connected in parallel to each other, each resistor being in a circuit leg including one or more field effect transistors capable of being switched directly between a non-conductive OFF condition and a fully conductive ON condition, and the resistor ladder network circuit or circuits having resistance values effective to maintain a measurement current of no more than 100 amps through molten metal present in the passage when the circuit or circuits are exposed to the discharge voltage from the one or more ultra-capacitors;

a controller adapted for individually switching the field effect transistors of the circuit legs of each resistor ladder network circuit between the non-conductive OFF condition and the fully conductive ON condition according to a sequence effective for maintaining the measurement current within a pre-determined current range at least for a time required for measurement of cleanliness of the molten metal; and an analyzer for analyzing the voltage signal, the analyzer comprising a computer-readable non-transitory storage medium storing statements and instructions, which, when executed by one or more processors, cause the one or more processors to:

sample digital data of measured voltage across the electrodes to generate data samples;

update a delayed running average of the data samples to establish a baseline for identifying sudden changes in amplitude of the data samples;

determine a threshold by adding a prescribed value to the baseline;

identify a possible inclusion when a significant number of data samples exceeds the threshold;

identify an end of the possible inclusion when a prescribed number of data samples fall below the threshold;

bypass a preset number of data samples when the end of the inclusion is identified, wherein bypassing the preset number of data samples includes not updating the delayed running average with the preset number of data samples; and compare a parameter of the possible inclusion with a lookup table to categorize the possible inclusion as either (i) an actual inclusion or (ii) noise.

* * * * *